United States Patent
Tamme et al.

(10) Patent No.: US 8,680,312 B2
(45) Date of Patent: Mar. 25, 2014

(54) PROCESS FOR CONVERSION OF DISILANES

(75) Inventors: Gudrun Tamme, Moritzburg OT Boxdorf (DE); Werner Geissler, Thiendorf OT Loetzschen (DE); Konrad Mautner, Burghausen (DE)

(73) Assignee: Wacker Chemie AG, Munich (DE)

( * ) Notice: Subject to any disclaimer, the term of this patent is extended or adjusted under 35 U.S.C. 154(b) by 17 days.

(21) Appl. No.: 13/582,642

(22) PCT Filed: Feb. 18, 2011

(86) PCT No.: PCT/EP2011/052440
§ 371 (c)(1),
(2), (4) Date: Sep. 4, 2012

(87) PCT Pub. No.: WO2011/107360
PCT Pub. Date: Sep. 9, 2011

(65) Prior Publication Data
US 2012/0330045 A1    Dec. 27, 2012

(30) Foreign Application Priority Data
Mar. 4, 2010    (DE) .......................... 10 2010 002 577

(51) Int. Cl.
*C07F 7/08*    (2006.01)
(52) U.S. Cl.
USPC ........................................................ 556/430

(58) Field of Classification Search
USPC ........................................................ 556/430
See application file for complete search history.

(56) References Cited

U.S. PATENT DOCUMENTS 5,292,912 A    3/1994    Chadwick et al.

FOREIGN PATENT DOCUMENTS

| EP | 325248 A2 * | 7/1989 |
| EP | 0635510 A1 | 1/1995 |
| JP | 7081920 A | 3/1995 |

OTHER PUBLICATIONS

Hideki Sakurai et al., "Aluminum Chloride-Catalyzed Reactions of Organosilicon Compounds II. Facile Syntheses of Alkylchlorosilanes, -Germanes, and _Stannanes (1 )", Tetrahedron Letters No. 45, pp. 5493-5497, 1966, Pergamon Press Ltd.

* cited by examiner

*Primary Examiner* — Johann R Richter
*Assistant Examiner* — Kofi Adzamli
(74) *Attorney, Agent, or Firm* — Brooks Kushman P.C.

(57) ABSTRACT

Highly alkyl-substituted disilanes generally considered as uncleavable, obtained as part of the residue of alkylchlorosilane synthesis, are converted into cleavable disilanes having fewer alkyl groups by reaction with hydrogen halide in the presence of an alumina catalyst. The resulting disilanes can be cleaved into commercially valuable monosilanes by conventional processes.

9 Claims, No Drawings

PROCESS FOR CONVERSION OF DISILANES

CROSS-REFERENCE TO RELATED APPLICATIONS

This application is the U.S. national phase of PCT Appln. No. PCT/EP2011/052440 filed Feb. 18, 2011, which claims priority to German Patent Application No. 10 2010 002 577.1 filed Mar. 4, 2010, which are incorporated herein by reference.

BACKGROUND OF THE INVENTION

1. Field of the Invention

The invention concerns the catalyzed elimination of alkyl groups from disilanes comprising chlorine groups and alkyl groups in the presence of hydrogen halides.

2. Description of the Related Art

The high-boiling fraction from the reaction of methyl chloride and silicon with a boiling point above 70° C. (high boilers) contains the so-called "cleavable disilanes" dimethyltetrachlorodisilane and trimethyltrichlorodisilane, which are simple to cleave with hydrogen halide into monosilanes under amine catalysis by following known processes. The other disilanes with four, five and six methyl groups cannot be utilized in this way and therefore are also known as "non-cleavable disilanes".

A multiplicity of patents relate to converting the high boilers into monomeric alkylchlorosilanes. The processes which have been described are all very costly and inconvenient and have high apparatus requirements. For example, EP 635510 A describes cleaving the high boilers into monosilanes by using hydrogen halide and a catalyst comprising aluminum chloride at temperatures above 250° C.

H. Sakurei et al. ("Aluminum chloride-catalyzed reactions of organosilicon compounds II", Tetrahedron Letters No. 45, pp. 5493-5497, 1966, Pergamon Press Ltd.) describe the batchwise conversion of disilanes in the liquid phase partly in the presence of acetyl chloride.

SUMMARY OF THE INVENTION

The invention provides a process for producing disilanes of general formula (1)

$$R_a Si_2 Cl_{6-a} \qquad (1),$$

which comprises reacting mixtures comprising the disilanes of general formula (2)

$$R_b Si_2 Cl_{6-b} \qquad (2),$$

where
R represents an alkyl radical of 1 to 6 carbon atoms,
a represents the values 1, 2 or 3,
b represents the values 4, 5 or 6,
with hydrogen halide in the presence of an alumina catalyst which, per 100 parts by weight of alumina, contains from 1 to 10 parts by weight of aluminum chloride and from 0 to 10 parts by weight of a metal oxide selected from magnesium oxide, copper oxide, zinc oxide and mixtures thereof.

DETAILED DESCRIPTION OF THE PREFERRED EMBODIMENTS

The inventive process thus makes it possible to utilize alkyl-rich disilanes, e.g., hexamethyldisilane, pentamethylchlorodisilane and tetramethyldichlorodisilane, in a simple, robust and continuous manner.

The process detaches the alkyl groups with hydrogen halide under Lewis acid catalysis to form the so-called cleavable disilanes, which can then be fed into the amine-catalyzed cleavage process. Since this reaction is exothermic, the only reactor requirement is that it ensure heat removal.

Hydrogen chloride is preferably used in the process as the hydrogen halide.

The radical R is preferably of 1 to 6 carbon atoms. The radical R is more particularly a methyl or ethyl radical. The silanes (2) can be present in any desired proportions relative to each or one another. They can similarly be present in mixtures with other vaporizable substances that do not disrupt the conversion.

Dialkyltetrachlorodisilane and trialkyltrichlorodisilane are preferred products.

The alumina can be alpha- or preferably gamma-alumina. The alumina catalyst can be used as a powder or preferably as a shaped article. The alumina catalyst preferably includes at least 1, more preferably at least 3 and preferably at most 10, more preferably at most 6 parts by weight of aluminum chloride per 100 parts by weight of alumina. The alumina catalyst may include up to 5 parts by weight, preferably up to 2 parts by weight of a metal oxide per 100 parts by weight of alumina. Any desired oxides or mixed oxides of the metals magnesium, copper and zinc can be used as metal oxides or mixed oxides. Magnesium oxide is particularly preferred.

The alumina catalyst preferably has a BET surface area of at least 100 m²/g, more preferably at least 230 m²/g and preferably at most 600 m²/g, and preferably has a pore volume of at least 0.2 cm³/g, more preferably at least 0.5 cm³/g and preferably at most 1.5 cm³/g.

The alumina catalyst used is preferably an alumina-metal oxide support material coated with aluminum chloride. The aluminum chloride coating can be produced in situ by activating the $Al_2O_3$ with hydrogen chloride.

The inventive process is carried out in excess hydrogen halide, preferably with not more than twice the hydrogen halide quantity resulting from stoichiometric calculation.

The process is preferably carried out at not less than 150° C., more preferably not less than 180° C., and most preferably not less than 200° C., and preferably not more than 370° C., more preferably not more than 350° C., yet more preferably not more than 280° C., and most preferably not more than 240° C. The process is preferably carried out at not less than 1 bar, more preferably not less than 2 bar, most preferably not less than 4 bar, and preferably not more than 30 bar, more preferably not more than 15 bar, and most preferably not more than 10 bar.

The process can be carried out batchwise, or preferably, continuously.

Any temperature-controllable apparatus that permits easy handling of the solid catalyst is useful as a reactor for the process. Particular preference is given to using tubular reactors equipped with heat transfer media circuits, which permit convenient temperature management.

The symbols in the formulae herein all have their meanings independently of each other or one another. The silicon atom is tetravalent in all formulae.

In the inventive and comparative examples hereinbelow, unless specifically stated otherwise, all amounts and percentages are by weight and all reactions are carried out at a pressure of 6.5 bar (abs.) and a temperature of 300° C.

The reactions in the examples were carried out using a tubular reactor heated by a heat transfer medium, having nominal width of 50 mm and containing one liter of catalyst extrudates comprising gamma-alumina and about 5 wt % of aluminum chloride, having a BET surface area of 200 m²/g and a pore volume of 0.5 cm³/g.

The catalyst in Example 3 additionally contained 0.8 wt % of Mg in the form of an oxide.

The silane fraction to be utilized, having a boiling range of 70-160° C., comprises a varying proportion of reactant components and by-products such as, for example various alkyl (C2 or greater)-methyl-chlorosilanes, chloromethylsiloxanes and hydrocarbons.

Example 1

A disilane fraction comprising 70% of a mixture of tetramethyldichlorodisilane, pentamethylchlorodisilane and hexamethyldisilane and also 30% of secondary components is reacted at a throughput rate of 0.9 mol/h of methyl groups to be detached (about 170 g/h) with a 1.6-fold hydrogen chloride excess at a 220° C. reactor shell temperature and 5.5 bar overpressure to give a disilane conversion of 96% into dimethyltetrachlorodisilane and trimethyltrichloro-disilane.

Example 2

A disilane fraction comprising 55% of a mixture of tetramethyldichlorodisilane, pentamethylchlorodisilane and hexamethyldisilane and also 45% of secondary components is reacted at a throughput rate of 0.75 mol/h of methyl groups to be detached (about 170 g/h) with a 1.6-fold hydrogen chloride excess at a 220° C. reactor shell temperature and 5.5 bar overpressure to give a disilane conversion of 77% into dimethyltetrachlorodisilane and trimethyltrichlorodisilane.

Example 3

A disilane fraction comprising 55% of a mixture of tetramethyldichlorodisilane, pentamethylchlorodisilane and hexamethyldisilane and also 45% of secondary components is reacted at a throughput rate of 0.66 mol/h of methyl groups to be detached (about 150 g/h) with a 2-fold hydrogen chloride excess at a 220° C. reactor shell temperature and 5.5 bar overpressure to give a disilane conversion of 87% into dimethyltetrachlorodisilane and trimethyltrichlorodisilane.

The invention claimed is:

1. A process for producing disilanes of the formula (1)

$$R_a Si_2 Cl_{6-a} \qquad (1),$$

comprising reacting a (a) mixture comprising disilanes of formula (2)

$$R_b Si_2 Cl_{6-b} \qquad (2),$$

where
R is an alkyl radical of 1 to 6 carbon atoms,
a is 1, 2 or 3,
b is 4, 5, or 6
b) with hydrogen chloride,
wherein reacting takes place in the presence of an alumina catalyst which, per 100 parts by weight of alumina, contains from 1 to 10 parts by weight of aluminum chloride and from 0 to 10 parts by weight of a metal oxide selected from magnesium oxide, copper oxide, zinc oxide and mixtures thereof; and wherein the temperature of reaction is in the range from 180° C. to 280° C.

2. The process of claim 1, wherein the radical R is a methyl or ethyl radical.

3. The process of claim 1, wherein the alumina catalyst has a pore volume of at least 0.2 cm³/g.

4. The process of claim 1, wherein the alumina catalyst has a pore volume of at least 0.5 cm³/g.

5. The process of claim 1, wherein the alumina catalyst has a BET surface area of at least 100 m²/g.

6. The process of claim 1, wherein the alumina catalyst has a BET surface area of at least 230 m²/g.

7. The process of claim 1, wherein the temperature of reacting is in the range of from 200° C. to 240° C.

8. The process of claim 1, wherein the pressure during reacting is from 1 bar to 30 bar.

9. The process of claim 1, wherein the pressure during reacting is from 4 bar to 10 bar.

* * * * *